United States Patent [19]

Bretherick et al.

[11] Patent Number: 4,497,717

[45] Date of Patent: Feb. 5, 1985

[54] COMPOSITIONS FOR USE IN OIL RECOVERY AND METHOD OF USE

[75] Inventors: Leslie Bretherick, Ascot; Philip K. G. Hodgson, Reading, both of England

[73] Assignee: The British Petroleum Company p.l.c., London, England

[21] Appl. No.: 363,865

[22] Filed: Mar. 31, 1982

[30] Foreign Application Priority Data

Apr. 1, 1981 [GB] United Kingdom ............... 8110210

[51] Int. Cl.$^3$ ............................................. E21B 43/22
[52] U.S. Cl. ............................... 252/8.55 D; 166/275; 260/501.13
[58] Field of Search ............... 252/8.55 D; 166/274, 166/275; 260/501.13; 544/157, 158, 171

[56] References Cited

U.S. PATENT DOCUMENTS

| | | | |
|---|---|---|---|
| 2,217,846 | 10/1940 | Orthner et al. | 260/501.13 |
| 3,448,128 | 6/1969 | Marumo et al. | 260/501.13 |
| 3,689,470 | 9/1972 | Shachat | 260/501.13 |
| 3,873,583 | 3/1975 | Walz et al. | 544/171 |
| 3,939,911 | 2/1976 | Maddox, Jr. et al. | 166/274 |
| 4,193,452 | 3/1980 | Wilson et al. | 166/274 |
| 4,216,097 | 8/1980 | Stournas | 252/8.55 D |

FOREIGN PATENT DOCUMENTS 1516284 7/1978 United Kingdom .

Primary Examiner—Herbert B. Guynn
Attorney, Agent, or Firm—Morgan, Finnegan, Pine, Foley & Lee

[57] ABSTRACT

Betaines containing the morpholine nucleus, some of which are novel per se, are dissolved in sea water or formation water, the concentration of betaine being from 200 to 100,000 ppm to give a surfactant solution suitable for displacing crude oil from a formation in an enhanced oil recovery process. Included in the solution can be an anionic surfactant containing in its structure an ethoxylated benzene ring which shows a synergistic effect with the betaine in lowering the interfacial tension of the surfactant solution against oil. These betaines have high tolerance towards divalent metal cations and high temperature stability as compared with betaines previously proposed for enhanced oil recovery.

3 Claims, No Drawings

COMPOSITIONS FOR USE IN OIL RECOVERY AND METHOD OF USE

This invention relates to surfactant compositions suitable for injection into an oil bearing formation, more particularly to low concentration surfactant compositions containing betaines and to a method of using same in the recovery of crude oil.

The displacement of oil in a formation by the use of betaine surfactants has been previously published in, for example, UK patent No. 1,516,284 and U.S. Pat. Nos. 3,939,911; 4,193,452 and 4,216,097.

It has now been found that a class of betaines derived from morpholine are particularly effective in the displacement of crude oil and superior in certain respects to betaines which have been previously described for this purpose.

According to the present invention an aqueous surfactant composition suitable for injection into an oil bearing formation to assist in the recovery of oil comprises an aqueous medium having dispersed therein a betaine of formula:

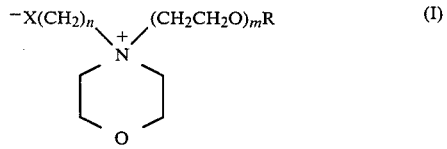

where
R is a $C_8$ to $C_{24}$ alkyl or $C_8$ to $C_{24}$ alkylphenyl which may optionally be substituted in inert substituents
m is 0 or an integer from 1 to 10
n is an integer from 1 to 5, and
$X^-$ is $CO_2^-$, $SO_3^-$ or $PO_3^=$.

The aqueous surfactant composition can be prepared by dispersing the betaine of formula (I) in the aqueous medium, preferably at a temperature above its Krafft point.

The betaines are suitable for use where the water in which the betaines are to be dispersed has a high concentration of cations and anions, as for example, sea water from the North Sea, or formation water with total ionic content up to 150,000 ppm including 50,000 ppm divalent ions.

Another aspect of the present invention is a method of oil recovery or injection well stimulation comprising injecting an aqueous surfactant composition of a betaine as hereinbefore described into an oil bearing formation.

The surfactant composition will usually be effective in displacing oil at a concentration of betaine as low as 200 ppm. There is no upper limit on the concentration of betaine that can be employed which can conveniently be up to 100,000 ppm.

A further aspect of this invention is that an anionic surfactant may be added to the above solution of the betaine to give a total concentration of betaine and anionic surfactant of 200 ppm to 100,000 ppm and the solution so produced may be used for oil recovery or injection well stimulation. Such anionic surfactants suitable for this application are represented by the formula:

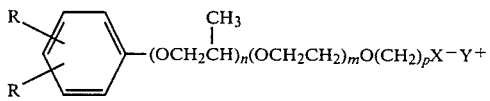

where
R is a $C_8$ to $C_{24}$ alkyl group, one of the R groups may be hydrogen and when both R groups are present they can be the same or different
n is an integer from 0 to 30
m is an integer from 2 to 18
p is an integer from 0 to 3
$X^-$ is $SO_3^-$, $CO_2^-$ or $PO_3^=$, and $Y^+$ is a cation.
Preferably $Y^+$ is a metal cation such as an alkali metal or ammonium including substituted ammonium.

The invention is illustrated by the following Examples:

EXAMPLE 1

Preparation of betaine formula:

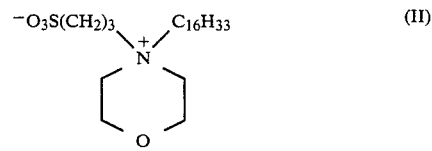

This betaine was prepared by the reaction of morpholine with 1-bromohexadecane at 150° C. for 1.25 hours to give 4-hexadecylmorpholine in 84% yield as a colourless distillable liquid, solidifying to a white solid on cooling. This reaction is described by M. Kerfanto in *Bull Soc. Chim. France* 1965, 3537 and in *Chemical Abstracts*, 1966, 65, 707g.

The 4-hexadecylmorpholine was then reacted with 1,3-propanesultone in 1,2-dichloroethane to give, after 9 hours at 90° C. N-hexadecyl-N-(3-sulphopropyl)-morpholinium hydroxide inner salt of formula (II) as a white powder in 48% yield. This reaction is described by N. Parris, J. K. Weil and W. M. Linfield in *J. Amer. Oil Chem. Soc.*, 1973, 50, 509.

The two reactions may be represented thus:

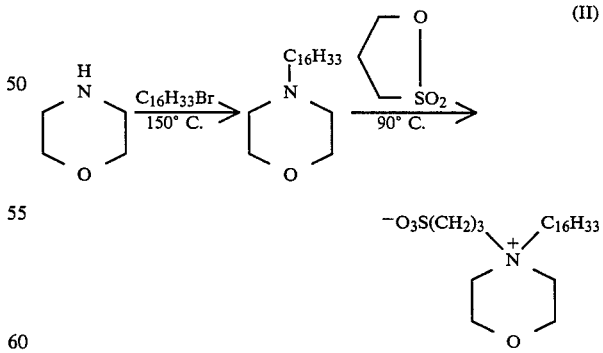

The compound (II) thus prepared was dissolved in filtered North Sea water at a temperature above its Krafft point (33° C.) to give a solution containing 2000 ppm. This solution was tested for its oil displacement capability as follows: a glass capillary of 1.3 mm internal diameter, 1 cm in length and sealed at one end was filled with Forties crude oil, and immersed in the solution of surfactant containing 2000 ppm. The time taken to release all the crude oil was measured at different temperatures of the solution. Compound (III) prepared in Example 2 was tested in the same way.

| Capillary oil release time | | |
|---|---|---|
| Compound (II) | 10 seconds at 33° C. | 4 seconds at 45° C. |
| Compound (III) | 60 seconds at 30° C. | 30 seconds at 40° C. |

Also measured was the Dynamic Interfacial Tension by the spinning drop method against Bothamsall crude oil.

| Dynamic Interfacial Tension in mNm$^{-1}$ at 43° C. | | |
|---|---|---|
| Compound (II) | 0.34 after 1 minute | 1.62 at equilibrium |
| Compound (III) | 0.15 after 5 minutes | 2.4 at equilibrium |

These results indicate that the compounds (II) and (III) will be effective in highly saline solutions in displacing oil from a reservoir.

EXAMPLE 2

Sand Column Test

A column containing 60 g of sand from the Forties field was prepared as follows:

The column was first flooded with formation water and then with Forties crude oil. The column was then flooded with the same formation water until no further oil was displaced to get a condition representing the post water flood residual oil saturation (SORW).

The column was then flooded with a 2000 ppm solution of the betaine of formula (II) at 70° C. in Forties sea water. It was found that the solution of betaine displaced oil from the column.

EXAMPLE 3

A betaine of formula:

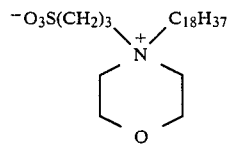 (III)

was prepared in a manner exactly as described in Example 1 except that 1-bromooctadecane was employed instead of the 1-bromohexadecane.

The compound (III) thus prepared was dissolved in filtered North Sea water at a temperature above its Krafft Point (40° C.) to give a solution containing 2000 ppm. This solution was tested as described above.

EXAMPLE 4

A betaine of formula

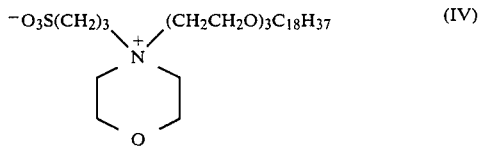 (IV)

was prepared in a manner exactly as described in Example 1 except that 1-bromo-3:6:9-trioxaoctacosane was used instead of the 1-bromohexadecane. The compound (IV) thus prepared was dissolved in filtered North Sea water at a temperature above 45° C. to give a solution containing 4000 ppm. This solution facilitated the release of Forties crude oil from the capillary in 100 seconds at 85° C. In a test to determine wettability characteristics betaine (IV) maintained Forties separator sand in a water wet state. The test involved contacting a droplet of Forties crude oil with separator sand in the presence of a solution of the betaine in sea water. As no sand adhered to the oil drop then the sand was deemed to be water-wet. Dynamic Interfacial Tension values of this solution at 96° C. against Forties crude oil were 0.866 mNm$^{-1}$ at equilibrium.

A mixture of such a solution of (IV) with a solution of the anionic surfactant (V) at 4000 ppm in filtered North Sea water gave a combined solution with good Dynamic Interfacial Tension values at 96° C. against Forties crude oil and improved the wettability and cloud point characteristics of the anionic surfactant. A similar solution of (IV) with (VI) had improved Dynamic Interfacial Tension values when compared with a solution of (VI) alone.

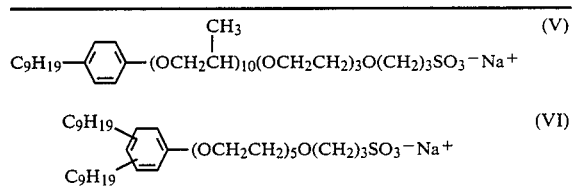

| Compound (IV)* | Compound (V)* | Cloud point | Equilibrium Dynamic Interfacial Tension in mNm$^{-1}$ at 96° C. (against Forties crude) |
|---|---|---|---|
| 1 | 3 | 55° C. | $3.98 \times 10^{-3}$ |
| 1 | 1 | 61° C. | $3.64 \times 10^{-3}$ |
| 3 | 1 | 100° C. | $4.24 \times 10^{-2}$ |
| 1 | 0 | — | 0.866 |
| 0 | 1 | 58° C. | $5.13 \times 10^{-4}$ |

| Compound (IV)* | Compound (VI)* | Equilibrium Dynamic Interfacial Tension in mNm$^{-1}$ at 96° C. |
|---|---|---|
| 1 | 3 | $1.02 \times 10^{-2}$ |
| 1 | 1 | $2.10 \times 10^{-2}$ |
| 3 | 1 | $4.71 \times 10^{-2}$ |
| 0 | 1 | $3 \times 10^{-2}$ |

*Solutions in filtered North Sea water at total surfactant concentration of 4,000 ppm. Figures indicate molar ratio of surfactants.

These results illustrate that a synergistic effect exists in that the interfacial tensions of the mixtures of Compound IV and Compound VI in the ratios of 1:3 and 1:1 are lower than either the pure compound IV or the pure compound VI.

The betaines of the present invention are characterised by high water solubility, high tolerance towards divalent metal cations, good temperature stability and wettability and are superior in these aspects to the majority of previously published betaine surfactants.

We claim:

1. A method of recovering crude oil from a formation which method comprises displacing the crude oil from the formation employing an aqueous surfactant composition wherein the surfactant composition comprises an aqueous medium having dispersed therein a surfactant wherein the surfactant is a betaine of formula:

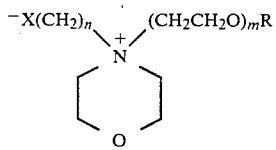

where
R is a $C_8$ to $C_{24}$ alkyl or $C_8$ to $C_{24}$ alkylphenyl which may optionally be substituted by inert substituents
m is an integer from 1 to 10
n is an integer from 1 to 5
and X is $CO_2^-$, $SO_3^-$ or $PO_3^=$.

2. A method according to claim 1 wherein the aqueous medium in which the betaine is dissolved is sea water or formation water having a total ionic content of up to 150,000 parts per million.

3. A method according to claim 1 wherein the aqueous surfactant composition additionally contains an effective amount of anionic surfactant of formula:

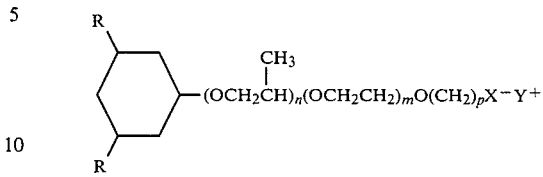

where
R is a $C_8$ to $C_{24}$ alkyl group
n is an integer from 0 to 30
m is an integer from 2 to 18
p is an integer from 0 to 3
$X^-$ is $SO_3^-$, $CO_2^-$, or $PO_3^=$
and $Y^+$ is a cation,
the total concentration of betaine and anionic surfactant being from 200 to 100,000 parts per million.

* * * * *